United States Patent [19]
Machonkin et al.

[11] Patent Number: 4,912,016
[45] Date of Patent: Mar. 27, 1990

[54] HIGH CONTRAST PHOTOGRAPHIC RECORDING MATERIAL AND EMULSION AND PROCESS FOR THEIR DEVELOPMENT

[75] Inventors: Harold I. Machonkin, Webster; Lee J. Fleckenstein; Donald L. Kerr, both of Rochester, all of N.Y.

[73] Assignee: Eastman Kodak Company, Rochester, N.Y.

[21] Appl. No.: 200,273

[22] Filed: May 31, 1988

[51] Int. Cl.$^4$ ............................................. G03C 1/06
[52] U.S. Cl. ................................. 430/264; 430/410; 430/598
[58] Field of Search ................. 430/264, 598, 410

[56] References Cited

U.S. PATENT DOCUMENTS

| | | | |
|---|---|---|---|
| 4,323,643 | 4/1982 | Mifune et al. | 430/441 |
| 4,429,036 | 1/1984 | Hirano et al. | 430/405 |
| 4,540,655 | 10/1985 | Takagi et al. | 430/410 |
| 4,681,836 | 7/1987 | Inoue et al. | 430/434 |

Primary Examiner—Roland E. Martin
Assistant Examiner—Janet C. Baxter
Attorney, Agent, or Firm—Thomas F. Kirchoff

[57] ABSTRACT

A photographic recording material and emulsion are described which are capable of providing high contrast images. The recording material and emulsion comprises negative working silver halide and contrast enhancing arylhydrazide nucleating agents. A process for utilization of the elements and emulsions is also described.

18 Claims, No Drawings

HIGH CONTRAST PHOTOGRAPHIC RECORDING MATERIAL AND EMULSION AND PROCESS FOR THEIR DEVELOPMENT

This invention relates to a high contrast photographic recording material and emulsion and to a process for obtaining a high contrast photographic image therefrom.

High contrast photographic images needed in the graphic arts and printing industries are generally obtained by developing a 'lith' emulsion (usually high in silver chloride content) in a hydroquinone, low sulphite, developer solution in the presence of one or more nucleating agents. The nucleating agents which have been very effective and which have found wide commercial acceptance are hydrazide compounds, particularly formylhydrazide compounds, and many such compounds have been proposed for incorporation in high contrast silver halide materials.

U.S. Pat. No. 4,323,643 describes various formylhydrazine compounds and their use in photographic recording materials for obtaining high contrast negative images having good dot quality and dot gradation. Included among these compounds are 1-substituted ureidophenyl-2-hydrazides which are developed in the presence of a dihydroxybenzene compound. While such compounds have enjoyed some level of commercial success, they do not provide the level of improvements desired in the art.

U.S. Pat. No. 4,681,836 describes a photographic recording material for forming high contrast negative images. The recording material comprises an acylhydrazide compound which may have an aliphatic acylamino group bonded to a hydrazide nitrogen atom. The recording material also comprises a rhodium compound in the silver halide emulsion layer. As is shown below by comparative data, aliphatic acylamino compounds of the '836 patent do not provide the contrast improvements which can be obtained with the present invention.

Accordingly, there is a continuing need for nucleating agents which are useful in providing desirable properties, particularly contrast levels, in high contrast photographic elements.

The present invention describes a photographic recording material capable of providing a high contrast silver image which comprises a support having thereon a negative-working photosensitive silver halide emulsion layer wherein said material also comprises a hydrazide compound having the structural formula:

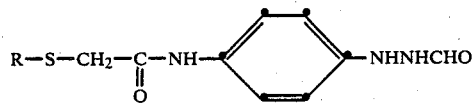

wherein:
R is alkyl having from 1 to about 8 carbon atoms or cycloalkyl having from 4 to about 8 carbon atoms in the ring.

The present invention also provides a photographic emulsion comprising a negative-working silver halide and a hydrazide nucleating agent having the structural formula:

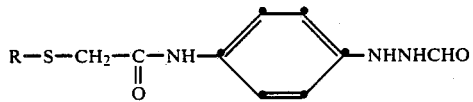

wherein:
R is alkyl having from 1 to about 8 carbon atoms or cycloalkyl having 4 to 8 carbon atoms in the ring.

Alkyl groups represented by R can be straight or branched chain. The preferred alkyl groups comprise from about 4 to about 8 carbon atoms. The alkyl and cycloalkyl groups can be substituted or unsubstituted. Substituents include halogen atoms (e.g., chlorine and fluorine), amino, including substituted amino (e.g., methylamino, ethylamino, dimethylamino), OH, SH, alkyl of from 1 to about 3 carbon atoms and aryl of from 6 to 10 carbon atoms.

Representative examples of hydrazide compounds which are suitable for use in this invention include:

Compound No.

1. 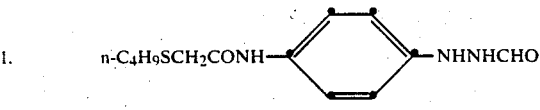

2. 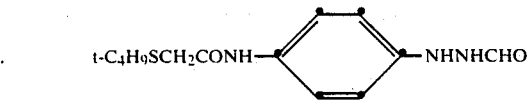

3. 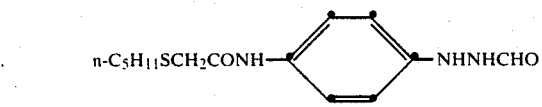

4. 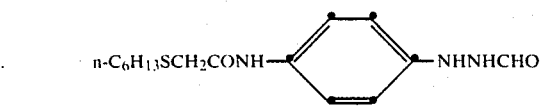

-continued 5. n-CH₂Cl(CH₂)₅SCH₂CONH—⟨C₆H₄⟩—NHNHCHO 6. n-C₇H₁₅SCH₂CONH—⟨C₆H₄⟩—NHNHCHO

7. CH₃C(CH₃)₂CH₂C(CH₃)₂SCH₂CONH—⟨C₆H₄⟩—NHNHCHO 8. n-C₈H₁₇SCH₂CONH—⟨C₆H₄⟩—NHNHCHO

9. ⟨S⟩—SCH₂CONH—⟨C₆H₄⟩—NHNHCHO

10. Cl—⟨S⟩—SCH₂CONH—⟨C₆H₄⟩—NHNHCHO

11. CH₃—⟨S⟩—SCH₂CONH—⟨C₆H₄⟩—NHNHCHO

12. C₂H₅SCH₂CONH—⟨C₆H₄⟩—NHNHCHO 13. i-C₃H₇SCH₂CONH—⟨C₆H₄⟩—NHNHCHO

14. ⟨C₆H₅⟩—CH₂SCH₂CONH—⟨C₆H₄⟩—NHNHCHO

Hydrazide compounds described herein can be prepared, for example, by reducing 1-formyl-2-(4-nitrophenyl)-hydrazide to the corresponding amine which is then caused to react with chloroacetic anhydride to yield a carbonamido substituted hydrazide which is then reacted with a mercapto compound to obtain a compound useful in this invention. This is illustrated by the following scheme:

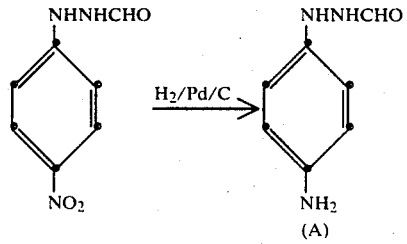

(A)

-continued

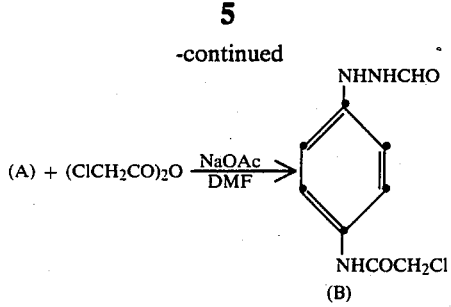

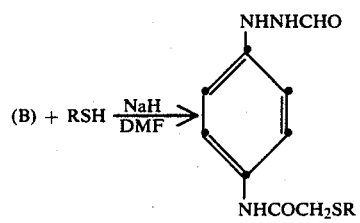

where R is as described above, NaOAc represents sodium acetate and DMF is N,N-dimethylformamide. This method is further illustrated in preparation of Compounds I and 9 as described above.

SYNTHESIS OF COMPOUND I

A solution of 1-butanethiol (3.9 g, 0.033 mol) in 50 mL of dry N,N-dimethylformamide (DMF) was cooled to 0° in an ice bath. Sodium hydride (1.3 g, 0.033 mol, 60% dispersion in mineral oil) was added in portions over a 15-20 minute period. Solid 2-[4-(chloroacetamido)phenyl]-1-formylhydrazine (6.83 g, 0.030 mol) was added, ice bath was removed, and the reaction mixture was stirred at room temperature for about one hour. The reaction mixture was added to ice water. The solid was separated by filtration, washed with water, then with heptane. Recrystallization (acetonitrile) gave 6.9 g (74%) of Compound I as tan crystals, mp 153°-155° C.

SYNTHESIS OF COMPOUND 9

A solution of cyclohexanethiol (2.6 g, 0.022 mol) in 50 mL of dry DMF was cooled to 0° in an ice bath. Sodium hydride (0.95 g, 0.024 mol, 60% dispersion in mineral oil) was added in portions over a 10-15 minute period. Solid 2-[4-chloroacetamido)phenyl]-1-formylhydrazine (4.55 g, 0.020 mol) was added and the reaction mixture was stirred for about one hour. The ice bath was removed and stirring was continued for about 16 hours at room temperature. The reaction mixture was added to ice water. The solid was separated by filtration and washed with water. Recrystallization (acetonitrile) gave 2.0 g (33%) of Compound 9 as tan crystals, mp 142-144° C.

The hydrazide nucleating agents described herein can be present in the photographic elements and emulsions of this invention in a concentration of from about $10^{-4}$ to about $10^{-1}$ mol thereof per mol of silver. A preferred quantity of the hydrazide compound is from $5 \times 10^{-4}$ to about $5 \times 10^{-2}$ mol per mol of silver. Optimum results are obtained when the hydrazide compound is present in a concentration of from about $8 \times 10^{-4}$ to about $5 \times 10^{-3}$ mol per mol of silver. The hydrazide compound can be incorporated in a photograhic silver halide emulsion layer or, alternatively, the hydrazide compound can be present in a hydrophilic colloid layer of the photographic element. Preferably, such hydrophilic colloid layer is coated contiguous to the emulsion layer in which the effects of the hydrazide compound are desired. The hydrazide compound can also be present in the photographic element in other layers such as subbing layers, interlayers or overcoating layers.

The present invention also provides a process for forming a high contrast photographic image which comprises developing a photographic recording material comprising a negative-working silver halide emulsion layer and a hydrazide nucleating compound having the following structural formula:

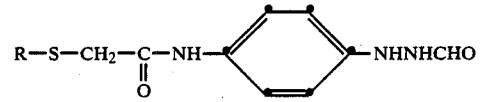

wherein:
R is alkyl having from 1 to about 8 carbon atoms or cycloalkyl having 4 to 8 carbon atoms in the ring.

The hydrazide compounds are employed in combination with negative-working photographic emulsions comprised of photosensitive siliver halide grains capable of forming a surface latent image and a binder. The silver halide emulsions include high chloride emulsions conventionally employed in forming lithographic photographic elements, as well as silver bromide and silver bromoiodide emulsions which are recognized in the art as being capable of attaining higher photographic speeds. Generally, the iodide content of the silver halide emulsions is less than about 10 mole percent silver iodide, based on total silver halide.

Silver halide grains suitable for use in the emulsions of this invention are capable of forming a surface latent image, as opposed to being of the internal latent image-forming type. Surface latent image silver halide grains are employed in the majority of negative-working silver halide emulsions, whereas internal latent image-forming silver halide grains, while capable of forming a negative image when developed in an internal developer, are usually employed with surface developers to form direct-positive images. The distinction between surface latent image and internal latent image silver halide grains is generally well recognized in the art.

Although the difference between a negative image produced by a surface latent image emulsion and a positive image produced by an internal latent image emulsion when processed in a surface developer is a qualitative difference which is visually apparent to even the unskilled observer, a number of tests have been devised to distinguish quantitatively surface latent image-forming from internal latent image-forming emulsions. For example, according to one such test when the sensitivity resulting from surface developer (A), described below, is greater than that resulting from internal developer (B), described below, the emulsion being previously light exposed for a period of from 1 to 0.01 second, the emulsion is of a type which is "capable of forming a surface latent image" or, more succinctly, it is a surface latent image emulsion. The sensitivity is defined by the following equation:

$$S = \frac{100}{Eh}$$

in which S represents the sensitivity and Eh represents the quantity of exposure necessary to obtain a mean density, i.e., $\frac{1}{2}(D_{max}+D_{min})$.

SURFACE DEVELOPER (A)

The emulsion is processed at 20° C. for 10 minutes in a developer solution of the following composition:

| | |
|---|---|
| N-methyl-p-aminophenol (hemisulfate) | 2.5 g |
| Ascorbic acid | 10 g |
| Sodium metaborate.4H$_2$O | 35 g |
| Potassium bromide | 1 g |
| Water to | 1 liter |

INTERNAL DEVELOPER (B)

The emulsion is processed at about 20° C. for 10 minutes in a bleaching solution containing 3 g of potassium ferricyanide per liter and washed with water for 10 minutes and developed at 20° C. for 10 minutes in a developer solution having the following composition:

| | |
|---|---|
| N-methyl-p-aminophenol (hemisulfate) | 2.5 g |
| Ascorbic acid | 10 g |
| Sodium metaborate.4H$_2$O | 35 g |
| Potassium bromide | 1 g |
| Sodium thiosulfate | 3 g |
| Water to | 1 liter |

The silver halide grains, when the emulsions are used for lith applications, have a mean grain size of not larger than about 0.7 micron, preferably about 0.4 micron or less. Mean grain size is well understood by those skilled in the art, and is illustrated by Mees and James, *The Theory of the Photograhic Process*, 3rd Ed., MacMillan 1966, Chapter 1, pp. 36-43. The photographic emulsions can be coated to provide emulsion layers in the photographic elements of any conventional silver coverage. Conventional silver coverages fall within the range of from about 0.5 to about 10 grams per square meter.

As is generally recognized in the art, higher contrasts can be achieved by employing relatively monodispersed emulsions. Monodispersed emulsions are characterized by a large proportion of the silver halide grains falling within a relatively narrow size-frequency distribution. In quantitative terms, monodispersed emulsions have been defined as those in which 90 percent by weight or by number of the silver halide grains are within plus or minus 40 percent of the mean grain size.

Silver halide emulsions contain, in addition to silver halide grains, a binder. The proportion of binder can be widely varied, but typically is within the range of from about 20 to 250 grams per mol of silver halide. Excessive binder can have the effect of reducing maximum densities and consequently also reducing contrast. For contrast values of 10 or more it is preferred that the binder be present in a concentration of 250 grams per mol of silver halide, or less.

The binders of the emulsions can be comprised of hydrophilic colloids. Suitable hydrophilic materials include both naturally occurring substances such as proteins, protein derivatives, cellulose derivatives, e.g., cellulose esters, gelatin, e.g., alkali-treated gelatin (pigskin gelatin), gelatin derivatives, e.g., acetylated gelatin, phthalated gelatin and the like, polysaccharides such as dextran, gum arabic, zein, casein, pectin, collagen derivatives, collodion, agar-agar, arrowroot, albumin and the like as described in U.S. Pat. Nos. 2,614,928; 2,614,929; 2,614,930; 2,691,582; 2,327,808; 2,448,534; 2,787,545; 2,956,880; 3,061,436; 2,816,027; 3,132,945; 3,138,461; 3,186,846; 2,960,405; 3,436,220; 3,486,896; 2,992,213; 3,157,506; 3,184,312; 3,539,353; 3,227,571; 3,532,502; 3,551,151; 3,923,517; 4,018,609; 2,110,491; 2,311,086; 2,343,650; 2,322,085; 2,563,791; 2,725,293; 2,748,022; 2,956,883; and U.K. Pat. Nos. 793,549; 1,167,159; 1,186,790; 1,483,551 and 1,490,644 which patent disclosures are incorporated herein by reference.

In addition to hydrophilic colloids the emulsion binder can be optionally comprised of synthetic polymeric materials which are water insoluble or only slightly soluble, such as polymeric latices. These materials can act as supplemental grain peptizers and carriers, and they can also advantageously impart increased dimensional stability to the photographic elements. The synthetic polymeric materials can be present in a weight ratio with the hydrophilic colloids of up to 2:1. It is generally preferred that the synthetic polymer materials constitute from about 20 to 80 percent by weight of the binder.

Suitable synthetic polymer materials can be chosen from among poly(vinyl lactams), acrylamide polymers, polyvinyl alcohol and its derivatives, polyvinyl acetals, polymers of alkyl and sulfoalkyl acrylates and methacrylates, hydrolyzed polyvinyl acetates, polyamides, polyvinyl pyridine, acrylic acid polymers, maleic anhydride copolymers, polyalkylene oxides, methacrylamide copolymers, polyvinyl oxazolidinones, maleic acid copolymers, vinylamine copolymers, methacrylic acid copolymers, acryloyloxyalkylsulfonic acid copolymers, sulfoalkylacrylamide copolymers, polyalkyleneimine copolymers, polyamines, N,N-dialkylaminoalkyl acrylates, vinyl imidazole copolymers, vinyl sulfide copolymers, vinyl sulfide copolymers, halogenated styrene polymers, amineacrylamide polymers, polypeptides and the like as described in U.S. Pat. Nos. 3,679,425; 3,706,564; 3,813,251; 2,253,078; 2,276,322; 2,276,323; 2,281,703; 2,311,058; 2,414,207; 2,484,456; 2,541,474; 2,632,704; 3,425,836; 3,415,653; 3,615,624; 3,488,708; 3,392,025; 3,511,818; 3,681,079; 3,721,565; 3,852,073; 3,861,918; 3,925,083; 3,879,205; 3,142,568; 3,062,674; 3,220,844; 2,882,161; 2,579,016; 2,829,053; 2,698,240; 3,003,879; 3,419,397; 3,284,207; 3,167,430; 2,957,767; 2,893,867; 2,869,986; 2,904,539; 3,929,482; 3,860,428; 3,939,130; 3,411,911; 3,287,289; 2,211,323; 2,284,877; 2,420,455; 2,533,166; 2,495,918; 2,289,775; 2,565,418; 2,865,893; 2,875,059; 3,536,491; 3,479,186; 3,520,857; 3,690,888; and 3,748,143, and U.K Pat. Nos. 808,227; 808,228; 822,192; 1,062,116; 1,398,055 and 1,466,600, which patent disclosures are incorporated herein by reference.

Although the term "binder" is employed in describing the continuous phase of the silver halide emulsions, it is recognized that other terms commonly employed by those skilled in the art, such as carrier or vehicle, can be interchangeably employed. The binders described in connection with the emulsions are also useful in forming undercoating layers, interlayers and overcoating layers of the photographic elements of this invention. Typically the binders are hardened with one or more photographic hardeners, such as those described in Paragraph VII, Product Licensing Index, Vol. 92, December 1971, Item 9232, which disclosure is hereby incorporated by reference.

Emulsions according to this invention having silver halide grains of any conventional geometric form (e.g., regular cubic or octahedral crystalline form) can be prepared by a variety of techniques, e.g., single-jet, double-jet (including continuous removal techniques), accelerated flow rate and interrupted precipitation techniques, as illustrated by Trivelli and Smith, *The Photographic Journal*, Vol. LXXIX, May, 1939, pp. 330–338, T. H. James, *The Theory of the Photographic Process*, 4th Ed., Macmillan, 1977, Chapter 3, Terwilliger et al Research Disclosure, Vol. 149, September 1976, Item 14987, as well as U.S. Pat. Nos. 2,222,264; 3,650,757; 3,672,900; 3,917,485; 3,790,387; 3,761,276 and 3,979,213, and German OLS No. 2,107,118 and U.K. Patent Publications 335,925; 1,430,465 and 1,469,480, which publications are incorporated herein by reference.

Double jet accelerated flow rate precipitation techniques are preferred for forming monodispersed emulsions. Sensitizing compounds, such as compounds of copper, thallium, cadmium, rhodium, tungsten, thorium, iridium and mixtures thereof, can be present during precipitation of the silver halide emulsion, as illustrated by U.S. Pat. Nos. 1,195,432; 1,951,933; 2,628,167; 2,950,972; 3,488,709; and 3,737,313, all incorporated herein by reference.

The individual reactants can be added to the reaction vessel through surface or sub-surface delivery tubes by gravity feed or by delivery apparatus for maintaining control of the pH and/or pAg of the reaction vessel contents, as illustrated by U.S. Pat. Nos. 3,821,002 and 3,031,304 and Claes et al, Photographische Korrespondenz, 102 Band, Number 10, 1967, p. 162. In order to obtain rapid distribution of the reactants within the reaction vessel, specially constructed mixing devices can be employed, as illustrated by U.S. Pat. Nos. 2,996,287; 3,342,605; 3,415,650; and 3,785,777; and German OLS Nos. 2,556,885 and 2,555,364. An enclosed reaction vessel can be employed to receive and to mix reactants upstream of the main reaction vessel, as illustrated by U.S. Pat. Nos. 3,897,935 and 3,790,386.

The grain size distribution of the silver halide emulsions can be controlled by silver halide grain separation techniques or by blending silver halide emulsions of differing grain sizes. The emulsions can include ammonical emulsions, as illustrated by Glafkides, *Photographic Chemistry*, Vol. 1, Fountain Press, London, 1958, pp. 365–368 and pp. 301–304; thiocyanate ripened emulsions, as illustrated by U.S. Pat. No. 3,320,069; thioether ripened emulsions, as illustrated by U.S. Pat. Nos. 3,271,157; 3,574,628 and 3,737,313 or emulsions containing weak silver halide solvents, such as ammonium salts, as illustrated by U.S. Pat. No. 3,784,381 and *Research Disclosure*, Vol. 134, June 1975, Item 13452.

The silver halide emulsion can be unwashed or washed to remove soluble salts. The soluble salts can be removed by chill setting and leaching, as illustrated by U.S. Pat. Nos. 2,316,845 and 3,396,027; by coagulation washing, as illustrated by U.S. Pat. Nos. 2,618,556; 2,614,928; 2,565,418; 3,241,969 and 2,489,341 and by U.K. Pat. Nos. 1,035,409 and 1,167,159; by centrifugation and decantation of a coagulated emulsion, as illustrated by U.S. Pat. Nos. 2,463,794; 3,707,378; 2,996,287 and 3,498,454; by employing hydrocyclones alone or in combination with centrifuges, as illustrated by U.K. Pat. Nos. 336,692 and 1,356,573; by diafiltration with a semipermeable membrane, as illustrated by *Research Disclosure*, Vol. 102, October 1972, Item 10208. The emulsions, with or without sensitizers, can be dried and stored prior to use as illustrated by *Research Disclosure*, Vol. 101, September 1972, Item 10152.

The silver halide emulsions can be chemically sensitized with active gelatin, as illustrated by T. H. James, *The Theory of the Photographic Process*, 4th Ed., Macmillan, 1977, pp. 67–76, or with sulfur, selenium, tellurium, platinum, palladium, iridium, osmium, rhenium or phosphorus sensitizers or combinations of these sensitizers, such as at pAg levels of from 5 to 10, pH levels of from 5 to 8 and temperatures of from 30° to 80° C., as illustrated by *Research Disclosure*, Vol. 134, June 1975, Item 13452. The emulsions need not be chemically sensitized, however, in order to exhibit the advantages of this invention.

The silver halide emulsions can be spectrally sensitized with dyes from a variety of classes, including the polymethine dye class, which includes the cyanines, merocyanines, complex cyanines and merocyanines (i.e., tri-, tetra- and polynuclear cyanines and merocyanines), oxonols, hemioxonols, styryls, merostyryls and streptocyanines.

By suitable choice of substituent groups the dyes can be cationic, anionic or nonionic. Preferred dyes are cationic cyanine and merocyanine dyes. Emulsions containing cyanine and merocyanine dyes have been observed to exhibit relatively high contrasts. Spectral sensitizing dyes specifically preferred for use in the practice of this invention are as follows:

SS-1: Anhydro-5,5'-dichloro-9-ethyl-3,3'-bis(3-sulfopropyl)oxacarbocyanine hydroxide, sodium salt
SS-2: 5,5',6,6'-Tetrachloro-1,1',3,3'-tetraethylbenzimidazolocarbocyanine iodide
SS-3: 3,3'-Diethyl-9-methylthiacarbocyanine bromide
SS-4: 3,3'-Diethyloxacarbocyanine iodide
SS-5: 5,5'-Dichloro-3,3',9-triethylthiacarbocyanine bromide
SS-6: 3,3'-Diethylthiocarbocyanine iodide
SS-7: 5,5'-Dichloro-2,2'-diethylthiocarbocyanine, p-toluene sulfonate salt
SS-8: 3-Carboxymethyl-5-[(3-methyl-2-thiazolidinylidene)-1-methylethylidene]rhodanine
SS-9: 3-Ethyl-3-[3-ethyl-2-thiazolidinylidene)-1-methylethylidene]rhodanine
SS-10: 5-[(3-(2-Carboxyethyl)-2-thiazolidinylidene)ethylidene]-3-ethylrhodanine
SS-11 1-Carboxymethyl-5-[(3-ethyl-2-benzothiazolinylidene)ethylidene]-3-phenyl-2-thiohydantoin
SS-12 1-Carboxymethyl-5-[(1-ethyl-2(H)-naphtho-[1,2-d]thiazolin-2-ylidene)ethylidene]-3-phenyl-2-thiohydantoin
SS-13: 3-Carboxymethyl-5-[(3-ethyl-2-benzothiazolinylidene)ethylidene]rhodanine
SS-14: 5-[(3-Ethyl-2-benzoxazolinylidene)ethylidene]-3-heptyl-2-thio-2,4-oxazolidinedione
SS-15: 3-Carboxymethyl-5-(3-ethyl-2-benzothiazolinylidene)rhodanine
SS-16: 3-Carboxymethyl-5-(3-methyl-2-benzoxazolinylidene)rhodanine
SS-17: 3-Ethyl-5-[(3-ethyl-2-benzoxazolinylidene)ethylidene]rhodanine.

The photographic elements can be protected against fog by incorporation of antifoggants and stabilizers in the element itself or in the developer in which the element is to be processed. Illustrative of conventional antifoggants and stabilizers useful for this purpose are those disclosed by Paragraph V, *Product Licensing Index*, Vol. 92, December 1971, Item 9232, which publication is hereby incorporated by reference.

It has been observed that fog reduction can be obtained by employing benzotriazole and antifoggants either in the photographic element or the developer in which the element is processed. The benzotriazole can be located in the emulsion layer or in any other hydrophilic colloid layer of the photographic element in a concentration in the range of from $10^{-4}$ to $10^{-1}$, preferably $10^{-3}$ to $3\times 10^{-2}$, mol per mol of silver. When the benzotriazole antifoggant is added to the developer, it is employed in a concentration of from $10^{-6}$ to about $10^{-1}$, preferably $3\times 10^{-5}$ to $3\times 10^{-2}$, mol per liter of developer.

Useful benzotriazoles can be chosen from among conventional benzotriazole antifoggants. These include benzotriazole (that is, the unsubstituted benzotriazole compound), halo-substituted benzotriazoles (e.g., 5-chlorobenzotriazole, 4-bromobenzotriazole and 4-chlorobenzotriazole) and alkyl-substituted benzotriazoles wherein the alkyl moiety contains from 1 to about 12 carbon atoms (e.g., 5-methylbenzotriazole).

In addition to the components of the photographic emulsions and other hydrophilic colloid layers described above it is appreciated that other conventional element addenda compatible with obtaining relatively high contrast images can be present. For example, addenda can be present in the described photographic elements and emulsions in order to stabilize sensitivity. Preferred addenda of this type include carboxyalkyl substituted 3H-thiazoline-2-thione compounds of the type described in U.S. Pat. No. 4,634,661. Also the photographic elements can contain developing agents (described below in connection with the processing steps), development modifiers, plasticizers and lubricants, coating aids, antistatic materials, matting agents, brighteners and color materials, these conventional materials being illustrated in Paragraphs IV, VI, IX, XII, XIII, XIV and XXII of *Product Licensing Index*, Vol. 92, December 1971, Item 9232, incorporated herein by reference.

The hydrazide compounds, sensitizing dyes and other addenda incorporated into layers of the photographic elements can be dissolved and added prior to coating either from water or organic solvent solutions, depending upon the solubility of the addenda. Ultrasound can be employed to dissolve addenda. Semipermeable and ion exchange membranes can be used to introduce addenda, such as water soluble ions (e.g., chemical sensitizers). Hydrophobic addenda, particularly those which need not be adsorbed to the silver halide grain surfaces to be effective, such as couplers, redox dye-releasers and the like, can be mechanically dispersed directly or in high boiling (coupler) solvents, as illustrated in U.S. Pat. Nos. 2,322,027 and 2,801,171, or the hydrophobic addenda can be loaded into latices and dispersed, as illustrated by *Research Disclosure*, Vol. 159, July 1977, Item 15930.

In forming photographic elements the layers can be coated on photographic supports by various procedures, including immersion or dip coating, roller coating, reverse roll coating, doctor blade coating, gravure coating, spray coating, extrusion coating, bead coating, stretch-flow coating and curtain coating. High speed coating using a pressure differential is illustrated by U.S. Pat. No. 2,681,294.

The layers of the photographic elements can be coated on a variety of supports. Typical photographic supports include polymeric film, wood fiber, e.g., paper, metallic sheet or foil, glass and ceramic supporting elements provided with one or more subbing layers to enhance the adhesive, antistatic, dimensional, abrasive, hardness, frictional, antihalation and/or other properties of the support surface.

Typical of useful polymeric film supports are films of cellulose nitrate and cellulose esters such as cellulose triacetate and diacetate, polystyrene, polyamides, homo- and co-polymers of vinyl chloride, poly(vinyl acetal), polycarbonate, homo- and copolymers of olefins, such as polyethylene and polypropylene, and polyesters of dibasic aromatic carboxylic acids with divalent alcohols, such as poly(ethylene terephthalate).

Typical of useful paper supports are those which are partially acetylated or coated with baryta and/or a polyolefin, particularly a polymer of an α-olefin containing 2 to 10 carbon atoms, such as polyethylene, polypropylene, copolymers of ethylene and propylene and the like.

Polyolefins, such as polyethylene, polypropylene and polyallomers, e.g., copolymers of ethylene with propylene, as illustrated by U.S. Pat. No. 4,478,128, are preferably employed as resin coatings over paper, as illustrated by U.S. Pat. Nos. 3,411,908 and 3,630,740, over polystyrene and polyester film supports, as illustrated by U.S. Pat. No. 3,630,742, or can be employed as unitary flexible reflection supports, as illustrated by U.S. Pat. No. 3,973,963.

Preferred cellulose ester supports are cellulose triacetate supports, as illustrated by U.S. Pat. Nos. 2,492,977; 2,492,978 and 2,739,069, as well as mixed cellulose ester supports, such as cellulose acetate propionate and cellulose acetate butyrate, as illustrated by U.S. Pat. No. 2,739,070.

Preferred polyester film supports are comprised of linear polyester, such as illustrated by U.S. Pat. Nos. 2,627,088; 2,720,503; 2,779,684 and 2,901,466.

The photographic elements can be imagewise exposed with various forms of energy, which encompass the ultraviolet and visible (e.g., actinic) and infrared regions of the electromagnetic spectrum as well as electron beam and beta radiation, gamma ray, X-ray, alpha particle, neutron radiation and other forms of corpuscular and wavelike radiant energy in either noncoherent (random phase) forms or coherent (in phase) forms, as produced by lasers. Exposures can be monochromatic, orthochromatic or panchromatic. Imagewise exposures at ambient, elevated or reduced temperatures and/or pressures, including high or low intensity exposures, continuous or intermittent exposures, exposure times ranging from minutes to relatively short durations in the millisecond to microsecond range and solarizing exposures, can be employed within the useful response ranges determined by conventional sensitometric techniques, as illustrated by T. H. James, *The Theory of the Photographic Process*, 4th Ed., Macmillan, 1977, Chapters 4, 6, 17, 18 and 23.

The light-sensitive silver halide contained in the photographic elements can be processed following exposure to form a visible image by associating the silver halide with an aqueous alkaline medium in the presence of a developing agent contained in the medium or the element. It is a distinct advantage of the present invention that the described photographic elements can be processed in conventional developers as opposed to specialized developers conventionally employed in conjunction with lithographic photographic elements to obtain very high contrast images. When the photographic elements contain incorporated developing agents, the elements can be processed in the presence of an activator, which can be identical to the developer in composition, but otherwise lacking a developing agent. Very high contrast images can be obtained at pH values in the range of from about 9.5 to about 12.3.

The developers are typically aqueous solutions, although organic solvents, such as diethylene glycol, can also be included to facilitate the solvency of organic components. The developers contain one or a combination of conventional developing agents, such as a polyhydroxybenzene, aminophenol, para-phenylenediamine, ascorbic acid, pyrazolidone, pyrazolone, pyrimidine, dithionite, hydroxylamine or other conventional developing agents. It is preferred to employ hydroquinone and 3-pyrazolidone developing agents in combination. The pH of the developers can be adjusted with alkali metal hydroxides and carbonates, borax and other basic salts. To reduce gelatin swelling during development, compounds such as sodium sulfate can be incorporated into the developer. Also, compounds such as sodium thiocyanate can be present to reduce granularity. Chelating and sequestering agents, such as ethylenediaminetetraacetic acid or its sodium salt, can be present. Generally, a wide variety of developer compositions can be employed in the practice of this invention. Specific illustrative photogra-phic developers are disclosed in the Handbook of Chemistry and Physics, 36th Edition, under the title "Photographic Formulae" at page 3001 et seq. and in Processing Chemicals and Formulas, 6th Edition, published by Eastman Kodak Company (1963), the disclosures of which are here incorporated by reference. The photographic elements can, of course, be processed with conventional developers for lithographic photographic elements, as illustrated by U.S. Pat. No. 3,573,914 and U.K. Pat. No. 376,600.

*Product Licensing Index* and *Research Disclosure* are published by Kenneth Mason Publications, Ltd., The Old Harbourmaster's, 8 North Street, Emsworth, Hampshire P010 7DD, ENGLAND.

The invention is further described by the examples illustrated below.

Each coating used in the following examples was prepared on a polyester support, using a monodispersed 0.25 μm AgBrI (3 mol % iodide) emulsion at 3.47 g/m² Ag, 2.24 g gel/m², and 0.96 g latex/m², where the latex was a copolymer of methyl acrylate, 2-acrylamido-2-methylpropane-sulfonic acid, and methyl methacrylate (88:5:7 monomer weight ratio). The silver halide emulsion was spectrally sensitized with 216 mg/Ag mol of anhydro-5,5'-dichloro-9-ethyl-3,3'-di-(3-sulfopropyl) oxacarbocyanine hydroxide, triethylamine salt. The nucleating agents were added as methanol solutions to the emulsion melts at a level of 2.0×10⁻³ mol/Ag mole. The emulsion layer was overcoated with gelatin containing polymethylmethacrylate beads.

EXAMPLE 1

Each coating described below in Table I was exposed for one second to a 3000° K. tungsten light source and processed for 80 seconds at 30° C. in the following developer solution:

| | |
|---|---|
| KOH, 45% | 12.4 g |
| K₂SO₃, 45% | 25 g |
| NaBr | 3.0 g |
| Hydroquinone | 15.0 g |
| Na₂CO₃ | 10.0 g |
| Ethylenediaminetetraacetic acid | 2.1 g |

-continued

| | |
|---|---|
| NaOH, 50% | 2.3 g |
| 3-(Diethylamino)-1,2-propanediol | 29.4 g |
| 1-Phenyl-4,4-dimethyl-3-pyrazolidone | 0.20 g |
| 1-Phenyl-5-mercaptotetrazole | 0.076 g |
| Phenethylpicolinium bromide | 2.8 g |
| 5-Methylbenzotriazole | 0.10 g |
| Nitrilomethylenephosphoric acid, pentasodium salt, 40% | 0.35 g |
| Water to | 1 liter | pH was measured as 10.9

Hydrazide compounds tested had the following structure:

Results are recorded in Table I

TABLE I

| Hydrazide Compound | R— | X— | Relative Speed[1] | Effective Contrast[2] |
|---|---|---|---|---|
| A | C₉H₁₉— | CO—<br>‖<br>O | 100 | 3.9 |
| B | C₆H₁₃ | CO—<br>‖<br>O | 125 | 5.5 |
| 1 Invention | C₄H₉— | S— | 209 | 17.9 |
| 4 Invention | C₆H₁₃— | S— | 195 | 18.1 |
| 8 Invention | C₈H₁₇— | S— | 155 | 8.4 |
| 9 Invention | (cyclohexyl-S) | S— | 240 | 30.2 |

Compounds A and B fall within the disclosure of U.S. Pat. No. 4,681,836
[1] Relative Speed is based on the speed of Compound A set at 100.
[2] Effective contrast is a measurement which represents the average slope between density values of 0.1 and 2.50.

From the data in Table I it can be seen that hydrazide nucleating agents useful in this invention yield improved relative speed and contrast values when compared with known prior art compounds.

The invention has been described in detail with reference to preferred embodiments thereof but it will be understood that variations and modifications can be effected within the spirit and scope of the invention.

What is claimed is:

1. A photographic recording material capable of providing a high contrast silver image which comprises a support having thereon a negative-working silver halide emulsion layer and a hydrazide compound having the following structural formula:

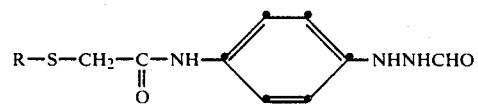

wherein:

R is alkyl having from 4 to about 8 carbon atoms or cyclohexyl.

2. The photographic recording material of claim 1 wherein R is a branched chain alkyl group.

3. The photographic recording material of claim 1 wherein the R alkyl or cyclohexyl group is substituted with halogen, amino, OH, SH or alkyl comprising from 1 to about 3 carbon atoms.

4. The photographic recording material of claim 1 wherein the hydrazide compound is present in an amount of from about $10^{-4}$ to about $10^{-1}$ mol thereof per mol of silver.

5. The photographic recording material of claim 4 wherein the hydrazide compound is present in an amount of from about $5 \times 10^{-4}$ to about $5 \times 10^{-2}$ mol thereof per mol of silver.

6. The photographic recording material of claim 1 wherein the hydrazide compound has the structural formula:

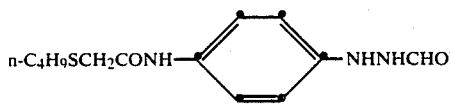

7. The photographic recording material of claim 1 having the structural formula:

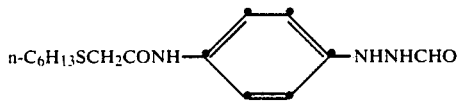

8. The photographic recording material of claim 1 having the structural formula:

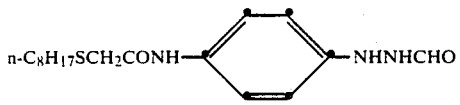

9. The photographic recording material of claim 1 having the structural formula:

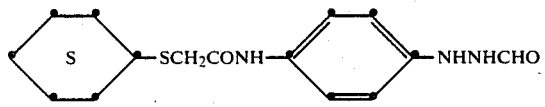

10. A photographic emulsion comprising negative working silver halide and a hydrazide nucleating compound having the following structural formula:

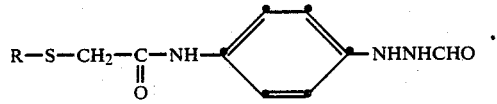

wherein:
R is alkyl having from 4 to about 8 carbon atoms or cyclohexyl.

11. The photographic emulsion of claim 10 wherein R is a branched chain alkyl group.

12. The photographic emulsion of claim 10 wherein the R alkyl or cyclohexyl group is substituted with halogen, amino, OH, SH or alkyl comprising from 1 to about 3 carbon atoms.

13. The photographic emulsion of claim 10 wherein the hydrazide compound is present in an amount of from about $10^{-4}$ to about $10^{-1}$ mol thereof per mol of silver.

14. The photographic emulsion of claim 13 wherein the hydrazide compound is present in an amount of from about $5 \times 10^{-4}$ to about $5 \times 10^{-2}$ mol thereof per mol of silver.

15. The photographic emulsion of claim 10 having the structural formula:

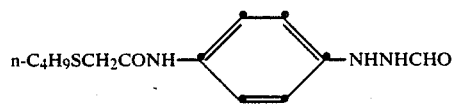

16. The photographic emulsion of claim 10 having the structural formula:

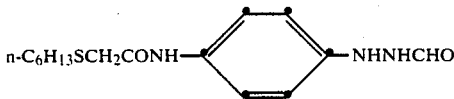

17. The photographic emulsion of claim 10 having the structural formula:

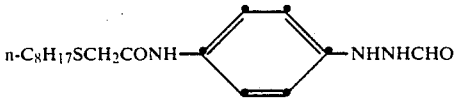

18. The photographic emulsion of claim 10 having the structural formula:

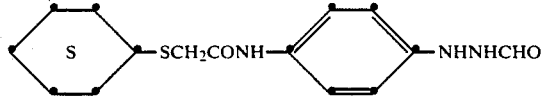

* * * * *